US005770729A

United States Patent [19]
Sasaoka et al.

[11] Patent Number: 5,770,729
[45] Date of Patent: Jun. 23, 1998

[54] OZONIDE REDUCING AGENT

[75] Inventors: Michio Sasaoka, Nakanokoshi; Daisuke Suzuki, Naruto; Takashi Shiroi, Itano-gun, all of Japan

[73] Assignee: Otsuka Kagaku Kabushiki Kaisha, Osaka, Japan

[21] Appl. No.: 530,292

[22] PCT Filed: Dec. 26, 1994

[86] PCT No.: PCT/JP94/02224

§ 371 Date: Jan. 22, 1996

§ 102(e) Date: Jan. 22, 1996

[87] PCT Pub. No.: WO95/18082

PCT Pub. Date: Jul. 6, 1995

[30] Foreign Application Priority Data

Dec. 28, 1993 [JP] Japan .................................... 5-338068

[51] Int. Cl.$^6$ .............................. C07B 31/00; C07B 33/00
[52] U.S. Cl. ..................... 540/353; 540/354; 540/359; 546/261; 549/59; 549/472; 549/473; 558/439; 568/38; 568/55; 568/57
[58] Field of Search ............................ 546/261; 549/472; 549/473, 59; 558/439; 568/38, 55, 57; 540/353, 354, 358

[56] References Cited

U.S. PATENT DOCUMENTS

| | | | |
|---|---|---|---|
| 3,722,752 | 3/1973 | Kenkare et al. | 222/145 |
| 3,978,021 | 8/1976 | Sagawa et al. | 260/45.9 KA |
| 4,035,383 | 7/1977 | Sweet | 260/314.5 |
| 4,203,757 | 5/1980 | Eiseman | 71/87 |
| 4,477,658 | 10/1984 | Scartazzini et al. | 544/16 |
| 4,764,299 | 8/1988 | Salomon | 252/48.2 |
| 4,940,808 | 7/1990 | Schulz et al. | 549/436 |
| 5,126,447 | 6/1992 | Torii et al. | 540/358 |
| 5,202,478 | 4/1993 | Schermanz et al. | 562/531 |
| 5,373,016 | 12/1994 | Brown et al. | 514/372 |

OTHER PUBLICATIONS

Tetrahedron Letters No. 36, 1996 pp. 4273–4278, A new and convenient method for converting olefins to aldehydes, James J. Pappas, et al.
Journal of the American Chemical Society, vol. 105, No. 25, Dec. 14, 1983, Washington, D.C., pp. 7345–7352, Synthesis of beta–lactam antibiotics by the sulpheno–cycloamination, M. Ihara, et al.
Abstract, Database WPI, Derwent Publication Ltd., London, BG; Class B05, AN 91–040134 XP002020277 & JP 02 306 973 A (Otsuka Pharmaceutical), Dec. 20, 1990.
Tetrahedron Letters vol. 32, No. 50, Dec. 9, 1991, Oxford, GB, pp. 7445–7448, A convenient synthesis of 2–exo–Methylene Penam, A potent intermediate of new β–lactam antibiotics synthesis, Hideo Tanaka, et al.
Tetrahedron vol. 37, No. 4, 1981, *Oxford, GB*, pp. 703–707, Synthesis of 2–oxocephalosporins, D. Hagiwara, et al.
Appell et al., New Reagents for the Reductive Quenching of Ozonolysis Reactions, Synthetic Communications, 25(22) pp. 3589–3595, 1995.

*Primary Examiner*—Mukund J. Shah
*Assistant Examiner*—Deepak R. Rao
*Attorney, Agent, or Firm*—Knobbe, Martens, Olson & Bear, LLP

[57] ABSTRACT

The present invention provides an ozonide reducing agent for use in the ozonolysis reaction of an organic compound, the ozonide reducing agent finding wide applications, and being safe and inexpensive from a commercial viewpoint and easy to treat for disposal.

The ozonide reducing agent of the invention is a compound wherein sulfur has, at both ends of its molecule, a hydrocarbon residue substituted by a polar functional group.

3 Claims, No Drawings

OZONIDE REDUCING AGENT

This is a 371 of PCT/JP94/02224 filed on Dec. 26, 1994.

TECHNICAL FIELD

The present invention relates to an ozonide reducing agent which is used for ozonolysis reaction of an organic compound, the reducing agent being useful for wide applications, safe and inexpensive from a commercial viewpoint and easy to treat for disposal.

BACKGROUND ART

Ozonolysis reaction has been widely commonly carried out as a method for preparing carboxylic acids, aldehydes, ketones and epoxides from organic unsaturated compounds or aromatic compounds. The reaction has been commonly resorted to for industrial purposes (Shin Jikken Kagaku Koza, vol. 15 [I-2], chap. 10, published on Sep. 20, 1975 by MARUZEN Co., Ltd.) Ozonolysis reaction is usually conducted by executing two steps, i.e., the step of causing ozone to act on an organic unsaturated compound or an aromatic compound to obtain an ozonide (peroxide) as an intermediate and the step of subjecting the ozonide to oxidization, reduction, hydrolysis and the like to obtain a stable object compound. The present invention relates to the latter step. The term "ozonide" used herein means any of the peroxides produced by ozonolysis reaction, such as α-ozonide, β-ozonide, hydroxyperoxide, diperoxide and the like. Since an ozonide is in constant danger of explosion and the like, the step of treating the ozonide to obtain a safe object compound in a high yield is presumably a key step for ozonolysis reaction. Generally, the mildest method of treating an ozonide scarcely entailing a side reaction is said to be a reductive decomposition (Shin Jikken Kagaku Koza, vol. 15 [I-2], chap. 10, published on September 20, 1975 by MARUZEN Co., Ltd.). Such method is carried out using various ozonide reducing agents. However, all of these reducing agents have some problems. The problems of respective reducing agents are given below in (1) to (7).

(1) Acetic acid-zinc reduction (J. Org. Chem., 25, 618 (1960)) is not applicable to a compound which is decomposed with an acid nor to a compound which must be decomposed at a low temperature. In addition, the reduction is not preferable since industrial wastes such as zinc oxide and the like are produced and cause environmental problems.

(2) Catalytic hydrogenation in the presence of a metallic catalyst such as Pt, Pd, Ni or the like (J. Am. Oil Chem. Soc., 42, 236 (1965)) always entails danger of explosion, since hydrogen is passed through a solution of a peroxide in the presence of a metal which is active to the solution. Further, when a halogen type solvent is used, the solvent as such is reduced by hydrogenation, and thus the kind of the solvent to be used is limited.

(3) In reduction with a metal such as Raney nickel, sodium boron hydride and the like (Can. J. Chem., 48, 1105 (1962)), the metal remains as industrial wastes after the treatment and poses environmental problems.

(4) In reduction with a trivalent phosphoric compound such as triphenylphosphine, phosphorous ester and the like (J. Org. Chem., 27, 4498 (1962)), phosphine oxide is not necessarily removed with ease from the reaction system after the treatment, while phosphorous ester produces a peculiar odor which presents an environmental problems. Further, the reduction is not advantageous in view of needs to consider environment and equipment, since a closed system may be needed to meet the strict standards for the drainage of phosphoric wastes.

(5) In reduction with dimethylsulfide which is most commonly used in laboratories (Tetrahedron Letters, 1966, 4273), the reducing agent exhibits a very high reducing power. However, this reducing agent is difficult to use for industrial purposes, since it causes an environmental problem of an offensive odor and involves difficulties of handling a compound with a low flash point.

(6) In reduction with dialkylsulfides and thiols (J. Org. Chem., 26, 4912 (1961)), the reducing agent can not find wide applications, since the agents exhibit a lower reducing power than the above-mentioned dimethylsulfide, produce a peculiar offensive odor, involve break of disulfide bond and side reactions such as addition reaction of thiol.

(7) Other sulfur-based ozonide reducing agents disclosed in literature and patents include, for example, thiourea (Tetrahedron Letters, 1983, 2367), sodium bisulfite (Helv. Chem. Acta., 21, 748 (1938)), sulfur dioxide (J. Am. Chem. Soc., 75, 3371 (1953)) and the like. Among them, thiourea and sodium bisulfite are used as dissolved in water and thus become frozen and useless when a low temperature is required, while sulfur dioxide causes an environmental problem associated with the emission of a sulfurous acid gas. Therefore, all of these reducing agents are disadvantageous.

As apparent from the above, an ozonide reducing agent has not been found out yet which is satisfactory in costs, safety, yield, facility of post-treatment, working atmosphere and the like, the reducing agent being usable under any reaction conditions.

DISCLOSURE OF THE INVENTION

The present invention has been accomplished in view of the above-mentioned problems of the conventional ozonide reducing agents in ozonolysis reaction.

Thus, an object of the present invention is to provide an ozonide reducing agent which can reductively decompose an ozonide in a wide range of reaction temperature in any reaction solvents without a side reaction.

Another object of the present invention is to provide an ozonide reducing agent which can be readily removed from the reaction system after the treatment and can give an object ozonolysis product in a high yield.

A further object of the present invention is to provide an ozonide reducing agent which does not require any additional equipment from viewpoints of environment and safety.

For solving the foregoing problems of conventional ozonide reducing agents in ozonolysis reaction, the present inventors directed their attention to sulfides which have the highest reducing power among organic reducing agents. Sulfides, typically dimethylsulfide, have two-coordinate sulfur and are easily oxidized by an active oxygen such as an ozonide (in other words, easily initiate reductive decomposition reaction of an ozonide) due to the electron-sharing resonance stabilization effect of the oxide (sulfoxide) (Shigeru Oae, Organic Sulfur Chemistry—Volume of Reaction Mechanism -, published on Sep. 1, 1982 by Kabushiki Kaisha Kagaku Dojin). However, although sulfides are expected to exhibit a high reducing power, they have the aforementioned problems of offensive odors and compounds with a low flash point. The present inventors conducted extensive research to solve these problems and found that when a polar functional group is introduced into sulfide, an object ozonide reducing agent can be obtained which maintains the high reducing power of sulfide and which has decreased offensive odor and improved safety due to the decreased steam pressure and elevated flash point. The present invention has been accomplished based on these novel findings.

Among the polar functional group-introduced sulfides, i.e., the compounds wherein a hydrocarbon residue substituted by a polar functional group such as hydroxyl, nitrile, carboxyl and the like is introduced into both ends of a molecule of two-coordinate sulfur, bis(hydroxy)alkylsulfide derivatives are widely used as, for example, an antioxidant for plastics such as polypropylene, polyester and the like (Japanese Unexamined Patent Publication No. 43536/1979), an antioxidant for lubricants (Japanese Unexamined Patent Publication No. 502093/1991), an antioxidant for inks and coating compositions (Japanese Unexamined Patent Publication No. 16916/1980), a softener for fibers (Japanese Examined Patent Publication No. 9968/1985), a pre-treating agent for catalysts (Japanese Unexamined Patent Publication No. 154394/1993) and the like. These compounds are industrially manufactured on a large scales and thus inexpensive. However, no report has been made on the use of bis(hydroxyalkyl) sulfide derivatives and mixtures thereof as an ozonide reducing agent for ozonolysis reaction.

The ozonide reducing agent of the present invention is a compound wherein sulfur has, at both ends of its molecule, a hydrocarbon residue substituted by a polar functional group.

The hydrocarbon residues at both ends of sulfur molecule in the ozonide reducing agent of the present invention may be the same or different. The polar functional group includes, for example, a hydroxyl group, a nitrile group, a carboxyl group and the like.

Examples of the ozonide reducing agent of the present invention include a compound represented by the formula

$$X-R^1-R^2-S-R^3-R^4-Y \quad (1)$$

wherein $R^1$ and $R^4$ are the same or different and each represents a single bond or an aliphatic hydrocarbon residue, $R^2$ and $R^3$ may be the same or different and each represents a saturated or unsaturated aliphatic hydrocarbon residue, an alicyclic hydrocarbon residue or an aromatic hydrocarbon residue and X and Y are the same or different and each represents a hydroxyl group, a nitrile group or a carboxyl group; a compound represented by the formula

$$R^5-S-R^6 \quad (2)$$

wherein $R^5$ and $R^6$ are the same or different and each represents a heterocyclic group having as a substituent at least one member selected from the class consisting of a hydroxyl group, a hydroxymethyl group, a nitrile group, a cyanomethyl group, a carboxyl group and a carboxymethyl group; and the like.

In the formula (1), the saturated or unsaturated aliphatic hydrocarbon residue represented by $R^2$ and $R^3$ includes, for example, a straight- or branched-chain $C_{1-6}$ alkylene group, a straight- or branched-chain $C_{2-8}$ alkenylene group, a straight- or branched-chain $C_{2-6}$ alkynylene group and the like. The straight- or branched-chain $C_{1-6}$ alkylene group includes, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene and the like. The straight- or branched-chain $C_{2-8}$ alkenylene group includes, for example, vinylidene, propenylene, pentylene, 4-propyl-2-pentylene and the like. The straight- or branched-chain $C_{2-6}$ alkynylene group includes, for example, ethynylene, propynylene and the like.

The alicyclic hydrocarbon residue represented by $R^2$ and $R^3$ includes, for example, $C_{3-8}$ cycloalkylene such as cyclopentylene, cyclohexylene and the like.

The aromatic hydrocarbon residue represented by $R^2$ and $R^3$ includes, for example, phenylene group which may be substituted by a $C_{1-6}$ alkyl group, such as a methyl group, an amino group and the like.

The aliphatic hydrocarbon residue represented by $R^1$ and $R^4$ includes, for example, a straight- or branched-chain $C_{1-6}$ alkylene group. Examples of the straight- or branched-chain $C_{1-6}$ alkylene group include methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene and the like.

Specific examples of the ozonide reducing agent represented by the formula (1) include bis(hydroxyalkyl)sulfide derivatives (more specifically, thiodimethanol, thiodiethanol, thiodipropanol, thiodiisopropanol, thiodi tertiary butanol, thiodipentanol, thiodihexanol, thiodiethylene glycol, thiodicyclopentanol, thiodicyclohexanol and the like), bis(hydroxyalkenyl)sulfide derivatives (more specifically, thiodivinyl alcohol, thiodipropenyl alcohol, thiodibutenyl alcohol, thiodipentenyl alcohol and the like), bis(hydroxyalkynyl)sulfide derivatives (more specifically, thiodipropargyl alcohol and the like), bis(hydroxyallyl) sulfide derivatives (more specifically, thiodiphenol, thiodicresol, bis(2-hydroxymethylphenyl)disulfide, bis(3-hydroxyethylphenyl)disulfide, bis(4-hydroxyallylphenyl) disulfide, thiodihydroxyaniline and the like), bis (cyanoalkyl)sulfide derivatives (more specifically, thiodipropionitrile, thiodibutyronitrile and the like), bis (cyanoalkenyl)sulfide derivatives (more specifically, thiodiacrylonitrile and the like), bis(carboxyalkyl)-sulfide derivatives (more specifically, thiodipropionic acid, thiodiisobutyric acid and the like), bis(carboxyalkenyl)sulfide derivatives (more specifically, thiodioleic acid, thiodifumaric acid and the like), hydroxyalkyl hydroxyalkenyl sulfide derivatives (more specifically, hydroxyethyl hydroxybutenyl sulfide and the like), hydroxyalkyl hydroxyalkynyl sulfide derivatives (more specifically, hydroxypropyl hydroxypropargyl sulfide and the like), hydroxyalkenyl hydroxyalkynyl sulfide derivatives (more specifically, hydroxypropenyl, hydroxypropargyl sulfide and the like), hydroxyalkyl carboxyalkyl sulfide derivatives (more specifically, hydroxyethyl carboxypropyl sulfide and the like), hydroxyalkyl cyanoalkyl sulfide derivatives (more specifically, hydroxyethyl cyanopropyl sulfide and the like), hydroxyalkyl 4-hydroxy-alkylphenyl sulfide derivatives (more specifically, hydroxyethyl 4-hydroxy-3-methylphenyl sulfide and the like), cyanoalkyl 4-hydroxyphenyl sulfide derivatives (more specifically, cyanoethyl 4-hydroxyphenyl sulfide and the like), cyanoalkyl cyanoalkenyl sulfide derivatives (more specifically, cyanopropyl cyanobutenyl sulfide and the like), cyanoalkyl carboxyalkyl sulfide derivatives (more specifically, cyanoethyl carboxypropyl sulfide and the like), cyanoalkyl carboxyalkenyl sulfide derivatives (more specifically, cyanoethyl carboxypropenyl sulfide and the like), cyanoalkenyl carboxyalkyl sulfide derivatives (more specifically, cyanobutenyl carboxypropyl sulfide and the like), cyanoalkenyl carboxyalkenyl sulfide derivatives (more specifically, cyanobutenyl carboxypropenyl sulfide and the like), cyanoalkenyl carboxyalkynyl, sulfide derivatives (more specifically, cyanobutenyl carboxypropargyl sulfide and the like), and the like. These compounds can be used singly or at least two of them can be used in mixture.

In the formula (2), the heterocyclic group constituting the heterocyclic group represented by $R^5$ and $R^6$ and having as a substituent at least one group selected from the class consisting of a hydroxyl group, a hydroxymethyl group, a nitrile group, a cyanomethyl group, a carboxyl group and a carboxymethyl group includes, for example, thienyl, furyl, pyridyl, pyranyl, pyrrolyl, chromenyl, imidazolyl, pyrazolyl, thiazolyl, oxazolyl, pyrazinyl, pyrimidyl, pyridazinyl, quinolyl and the like.

Specific examples of the ozonide reducing agent represented by the formula (2) include bis(hydroxyheterocyclic) sulfide derivatives (more specifically, thiodihydroxythiophene, thiodihydroxymethylthiophene, thiodihydroxyfuran, thiodihydroxymethylfuran, thiodihydroxypyridine, thiodihydroxymethylpyridine and the like). These compounds can be used singly or at least two of them can be used in mixture.

It is also possible to use a compound of the formula (1) and a compound of the formula (2) in combination.

The starting material to be subjected to the ozonolysis reaction in the practice of the present invention includes all of the organic compounds having in the molecule a carbon-carbon or carbon-nitrogen unsaturated bond, such as alkenes, alkynes, aromatic compounds and heterocyclic aromatic compounds, as described in Shin Jikken Kagaku Koza, vol. 15 [I-2], chap. 10 (published on Sep. 20, 1975 by MARUZEN Co., Ltd.). Specific examples are substituted ethylenes, steroids, enol ethers, azines, diazoalkanes, Shiff bases and the like, and more specifically, indene, styrene, cyclohexene, cyclohexylidene, camphene, longiolefin, norbornene, naphthoquinone, vinylcyclohexene, α-pinene, benzene, naphthalene, phenanthrene, anthracene, phenol, quinoline, pyrrole, furan, thiophene, indole, benzofuran, diphenylethylcarbinol, nitron, acetal and the like. Since the ozonide reducing agent of the present invention can be handled at around a neutrality, it can be applied to β-lactam compounds having an unsaturated bond at the side chains. Specific examples of such compounds include those disclosed in Japanese Unexamined Patent Publication 306973/1990 such as bicyclic oxazolinoazetidinone derivatives, bicyclic thiazolinoazetidinone derivatives, monocyclic azetidinone derivatives, monocyclic exo-methylene cephem derivatives, monocyclic exo-methylene penam derivatives and the like.

For carrying out the ozonization reaction, the conditions described, for example, in Shin Jikken Kagaku Koza, vol. 15 [I-2], chap. 10 (published on Sep. 20, 1975 by Maruzen Co., Ltd.) are widely employable. Stated more specifically, the ozonization reaction is carried out in an appropriate solvent. Usable solvents include, for example, alcohols such as methanol, ethanol, propanol, isopropanol, butanol, tert-butanol and the like, lower alkyl esters of lower carboxylic acid such as methyl formate, ethyl formate, propyl formate, butyl formate, methyl acetate, ethyl acetate, propyl acetate, butyl acetate, methyl propionate, ethyl propionate and the like, ketones such as acetone, methyl ethyl ketone, methyl propyl ketone, methyl butyl ketone, methyl isobutyl ketone, diethyl ketone and the like, ethers such as diethyl ether, ethyl propyl ether, ethyl butyl ether, dipropyl ether, diisopropyl ether, dibutyl ether, methyl cellosolve, dimethoxyethane and the like, cyclic ethers such as tetrahydrofuran, dioxane, 1,3-dioxolane and the like, acetonitrile, propionitrile, butyronitrile, isobutyronitrile, valeronitrile and the like, substituted or unsubstituted aromatic hydrocarbons such as benzene, toluene, xylene, chlorobenzene, anisole and the like, halogenated hydrocarbons such as dichloromethane, chloroform, dichloroethane, trichloroethane, dibromoethane, propylene dichloride, carbon tetrachloride, flons and the like, aliphatic hydrocarbons such as pentane, hexane, heptane, octane and the like, cycloalkanes such as cyclopentane, cyclohexane, cycloheptane, cyclooctane and the like, amides such as dimethylformamide, dimethylacetoamide and the like, dimethylsulfoxide and the like. These organic solvents can be used singly or in mixture with each other, and may contain water when required.

It is preferred that these solvents be used in an amount of about 1 to 200 liters, more preferably 2 to 100 liters, per kg of the starting material. The reaction is carried out at a reaction temperature of usually about −78° to 40° C., preferably about −60° to 10° C. The amount of ozone for use in the reaction may be 1 equivalent based on the starting material. When required, it is preferred to further pass the ozone until all the starting material is consumed. When ozone is used in an amount exceeding 1 equivalent, dry nitrogen is preferably passed through the reaction mixture to replace the excess ozone before post-treatment.

The reduction of the ozonization product (ozonide) according to the present invention is carried out by directly adding the ozonide reducing agent of the invention to the above-mentioned ozonization reaction solution. The amount of the ozonide reducing agent is at least 1 equivalent, preferably about 1 to 3 equivalents, based on the starting material to be subjected to the ozonolysis reaction.

It is preferred to conduct the ozonide reduction procedure according to the present invention at a temperature of about −76° to 100° C., preferably −40° to 30° C. When the temperature is higher, it is likely that the risk of explosion increases and the yield decreases. On the other hand, if the treating temperature is lower, it is likely that the reduction rate decreases and a larger amount of the reducing agent is required. It is suitable that the treating time is about 3 minutes to 12 hours, preferably about 30 minutes to 6 hours.

After completion of the reduction procedure, the sulfoxide (an oxide of the ozonide reducing agent of the invention) can be easily removed from the reaction system by water washing or filtration, since the sulfoxide is soluble in water and has a high crystallizability. Thus, the object product can be obtained in a substantially pure form by concentrating and crystallizing the reaction mixture. However, it is a matter of course that the reaction mixture can be purified by other methods. The sulfoxide resulting from the ozonide reducing agent can be disposed of by incineration.

The ozonide reducing agent of the present invention is a compound which is soluble in any of solvents (aqueous, nonaqueous, polar and nonpolar solvents) and maintains the homogeneous state in a wide temperature range (−76° to 40° C.). Therefore, use of the compound is scarcely limited by reaction conditions. Further, since drainage of sulfur compounds is not so strictly controlled as that of phosphoric compounds and the reducing agent scarcely produces the odor peculiar to sulfur compounds, the reducing agent requires no additional equipment for the protection of environment.

In addition, since a two-coordinate sulfur compound is characteristically oxidized with ease, the object product can be obtained in improved yields under mild conditions. Further, the reaction system can be easily handled as a hazardous material and with substantially no risk of explosion.

After completion of the reaction, the ozonide reducing agent as such is converted to a sulfoxide which can be readily separated from the organic solvent by water washing with no potential of adversely affecting the post-treatment. Further, the removed sulfoxide can be incinerated for disposal. The ozonide reducing agent of the present invention has many advantages compared with the above-mentioned conventional ozonide reducing agents for ozonolysis reaction.

BEST MODE FOR CARRYING OUT THE INVENTION

The following Examples illustrate the use of ozonide reducing agents of the present invention to clarify the present invention in further detail. However, the scope of the invention is not limited by the Examples.

EXAMPLE 1

Production of p-methoxybenzyl 2-(4-benzenesulfonylthio-3-phenylacetoamide-2-azetidinone-1-yl)-3-hydroxy-2-butenoate 2

A 1000 ml quantity of methylene chloride and 75 ml of isopropyl alcohol were added to 193 g of p-methoxybenzyl 2-(4-benzenesulfonylthio-3-phenylacetoamide-2-azethidinone-1-yl)-3-methyl-3-butenoate 1 (purity of 97.3%, 315.5 mmols) and stirred to obtain a solution. The reaction mixture was cooled to −15° C. after which an ozone gas (3 g $O_3$/hr) was introduced at −20° to 15° C. over a period of 5.5 hours. The excess ozone gas was removed using nitrogen gas, followed by addition of 40 ml of thiodiethanol at −10° C. The mixture was stirred for 12 hours while being warmed to room temperature. The reaction mixture was filtered to remove the precipitated thiodiethanol sulfoxide. Then the organic layer was concentrated under reduced pressure. A 1200 ml quantity of a 10% aqueous solution of isopropyl alcohol was added to the residue. The mixture was cooled to 24° C. or less for crystallization. Subsequently, 440 ml of water was added to obtain crystals, and the mixture was aged at 10° C. for one hour with stirring. The crystals were then collected by filtration, washed successively with an aqueous solution of isopropyl alcohol and cold isopropyl alcohol and dried, giving 186.3 g of the title compound 2 as crystals (purity of 98%) in a yield of 97%. The $^1$H-NMR spectrum of the compound was the same as that of an authentic sample.

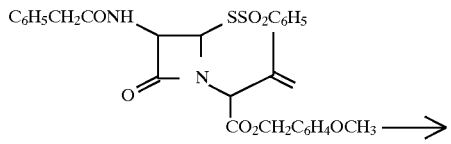

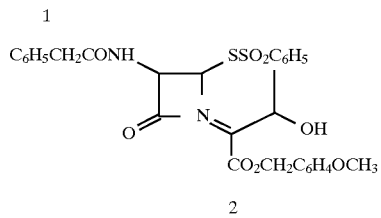

EXAMPLE 2

Production of diphenylmethyl 2-(4-benzenesulfonylthio-3-phenylacetoamide-2-azetidinone-1-yl)-3-hydroxy-2-butenoate 4

A 1000 ml quantity of methylene chloride and 75 ml of isopropyl alcohol were added to 211 g of diphenylmethyl 2-(4-benzenesulfonylthio-3-phenylacetoamide-2-azethidinone-1-yl)-3-methyl-3-butenoate 3 (purity of 98.2%, 323.2 mmol) and stirred to obtain a solution. The reaction mixture was cooled to −15° C. after which an ozone gas (3 g $O_3$/hr) was introduced at −20° to 15° C. over a period of 5.5 hours. The excess ozone gas was removed using nitrogen gas, followed by addition of 40 ml of thiodiethanol at −10° C. The mixture was stirred for 12 hours while being warmed to room temperature. The reaction mixture was washed with 400 ml of water to remove the precipitated thiodiethanol sulfoxide. Then the organic layer was concentrated under reduced pressure. A 1200 ml quantity of a 10% aqueous solution of isopropyl alcohol was added to the residue after which the mixture was cooled to 24° C. or less for crystallization. Subsequently, 440 ml of water was added to obtain crystals, and the mixture was aged at 10° C. for one hour with stirring. The crystals were then collected by filtration, washed successively with an aqueous solution of isopropyl alcohol and cold isopropyl alcohol and dried, giving 201.4 g of the title compound 4 as crystals (purity of 98%) in a yield of 95%. The $^1$H-NMR spectrum of the compound was the same as that of an authentic sample.

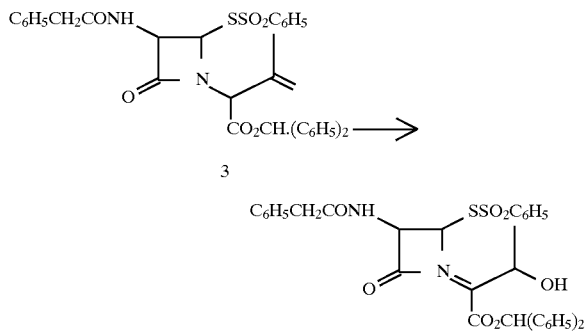

EXAMPLES 3 TO 12

The object alcohol 2 was prepared by carrying out the same reaction under the same conditions as in Example 1 with the exception of using the ozonide reducing agents and solvents shown in Table 1 and employing the reaction temperatures shown in the table. The results of the reaction are given in Table 1.

TABLE 1

| Ex. | Starting material | Ozonide reducing agent | Solvent | Reaction temperature | Object enol (yield) |
|---|---|---|---|---|---|
| 3 | 1 | Thiodiethanol | Same as in Ex. 1 | −76° C. | 2 (97%) |
| 4 | " | " | Same as in Ex. 1 | 0 to 5° C. | " (93%) |
| 5 | " | " | $CH_2Cl_2$ | −46 to −35° C. | " (92%) |
| 6 | " | " | Acetone | " | " (90%) |
| 7 | " | " | Toluene | " | " (90%) |
| 8 | " | Thiodipropanol | Same as in Ex. 1 | Same as in Ex. 1 | " (94%) |
| 9 | " | Thiodiisopropanol | Same as in Ex. 1 | Same as in Ex. 1 | " (95%) |
| 10 | " | Thiodicresol | Same as in Ex. 1 | Same as in Ex. 1 | " (93%) |
| 11 | " | Thiodipropionitrile | Same as in Ex. 1 | Same as in Ex. 1 | " (92%) |
| 12 | " | Thiodipropionic acid | Same as in Ex. 1 | Same as in Ex. 1 | " (89%) |

EXAMPLES 13 TO 18

The object alcohol 4 was prepared by carrying out the same reaction under the same conditions as in Example 2 with the exception of using the solvents shown in Table 2 and employing the reaction temperatures shown in the table. The results of the reaction are given in Table 2.

TABLE 2

| Ex. | Starting material | Ozonide reducing agent | Solvent | Reaction Temperature | Object enol (yield) |
|---|---|---|---|---|---|
| 13 | 3 | Thiodiethanol | $CH_2Cl_2$/methanol = 10/1 (v/v) | −45° C. to −35° C. | 4 (97%) |
| 14 | " | " | $CH_2Cl_2$/ethanol = 10/1 (v/v) | " | " (98%) |
| 15 | " | " | $CH_2Cl_2$/n-propyl alcohol = 10/1 (v/v) | " | " (97%) |
| 16 | " | " | $CH_2Cl_2$/isobutanol = 10/1 (v/v) | " | " (90%) |
| 17 | " | " | $CH_2Cl_2$/tert-butanol = 10/1 (v/v) | " | " (91%) |
| 18 | " | " | $CH_2Cl_2$/HO(CH$_2$)$_2$OH = 10/1 (v/v) | " | " (90%) |

EXAMPLE 19

Production of diphenylmethyl 1-(3-benzyl-2-thia-4,7-diazabicyclo[3.2.0]hepto-3-ene-6-one-7-yl)-3-hydroxy-2-butenoate 6

A 250 ml quantity of methylene chloride and 25 ml of isopropyl alcohol were added to 50 g of diphenylmethyl 1-(3-benzyl-2-thia-4,7-diazabicyclo-[3.2.0]hepto-3-ene-6-one-7-yl)-3-methyl-3-butenoate 5 and stirred to obtain a solution. The reaction mixture was cooled to −15° C. after which an ozone gas was introduced over a period of 1 hour and 40 minutes. After the excess ozone gas was removed using nitrogen gas, 11 ml of thiodiethanol and 12 ml of thiodipropionitrile were added at −10° C. The mixture was warmed to room temperature and stirred for 3 hours. The reaction mixture was filtered to remove the precipitated thiodiethanol sulfoxide, washed once with 200 ml of 5% aqueous sodium bicarbonate and twice with 100 ml of water, dried over anhydrous magnesium sulfate and concentrated under reduced pressure, giving 40 g of the title compound 6. The $^1$H-NMR spectrum of the compound was the same as that of an authentic sample.

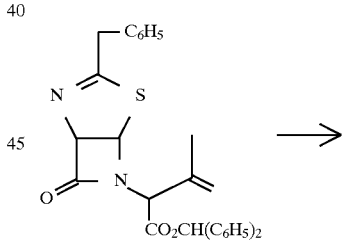

5

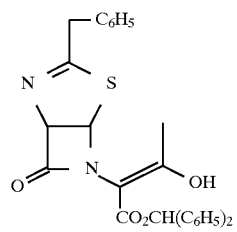

6

EXAMPLE 20

Production of p-nitrobenzyl 1-(4-formyl-3-(4-nitrophthalimide)-2-azetidinone-1-yl)-3-hydroxy-2-butenoate 8

A 100 ml quantity of methylene chloride and 7.5 ml of isopropyl alcohol were added to 20.1 g of p-nitrobenzyl 1-(4-formyl-3-(4-nitrophthalimide)-2-azetidinone-1-yl)-3-methyl-3-butenoate 7 and suspended. The reaction mixture was cooled to −15° C. after which an ozone gas was introduced over a period of 30 minutes. The excess ozone gas was removed using nitrogen gas, 6.2 ml of thiodiethanol was added, and the mixture was stirred for 1.5 hours while being warmed to room temperature. The reaction mixture was washed once with 200 ml of 5% aqueous sodium bicarbonate and twice with 200 ml of water, dried over anhydrous magnesium sulfate and pulverized using 500 ml of isopropyl ether, giving 15 g of the title compound. The $^1$H-NMR spectrum of the compound was the same as that of an authentic sample.

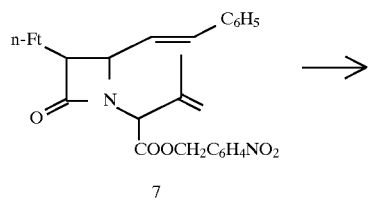

7

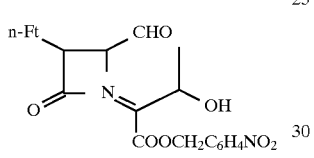

8 n-Ft:nitrophthalimide

EXAMPLE 21

Production of 1-(4-methoxyphenyl)azetidine-2,3-dione 10

A 100 ml quantity of methylene chloride and 7.5 ml of isopropyl alcohol were added to 20 g of 1-(4-methoxyphenyl)3-methylene azetidine-2-one 9 and dissolved with stirring. The reaction mixture was cooled to −15° C. after which an ozone gas was introduced over a period of 30 minutes. The excess ozone gas was removed using nitrogen gas and 3 ml of thiodiethanol and 6 g of thiodicresol were added, while being warmed to room temperature and then stirred for 1 hour. The reaction mixture was filtered to remove the precipitated thiodiethanolsulfoxide and washed once with 5% aqueous sodium bicarbonate and twice with 50 ml of water, dried over anhydrous magnesium sulfate and concentrated under reduced pressure, giving 14 g of the title compound 10. The $^1$H-NMR spectrum of the compound was the same as that of an authentic sample.

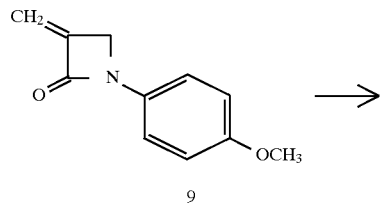

9

-continued

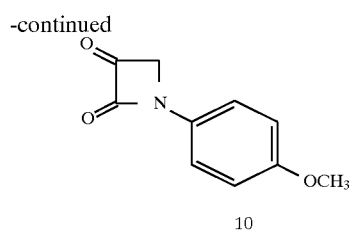

10

EXAMPLES 22 TO 39

Ozonolysis reaction was carried out using the reducing agents and starting materials represented by the following formulas. The conditions and results of the reaction are given in Table 3.

[Ozonide reducing agent]

HOCH$_2$CH$_2$SCH$_2$CH$_2$OH  (A)

HOCH$_2$CH$_2$CH$_2$SCH$_2$CH$_2$CH$_2$OH  (B)

NCCH$_2$CH$_2$CH$_2$SCH$_2$CH$_2$CH$_2$CN  (C)

(D)

HO—⟨◯⟩—S—⟨◯⟩—OH, (E)

HO—⟨◯⟩—S—⟨◯⟩—OH
       |         |
      CH$_3$    CH$_3$

[Starating material]

$$\underset{H}{\overset{H_5C_2}{\diagdown}}C=C\underset{C_2H_5}{\overset{H}{\diagup}} \quad (1)$$

$$\underset{CH_3}{\overset{CH_3}{\diagdown}}C=C\underset{COOCH_3}{\overset{CH_3}{\diagup}} \quad (2)$$

(3)

(4)

(5)

R:H or CH$_3$

-continued
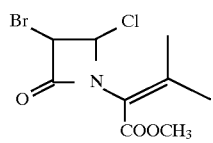 (6)
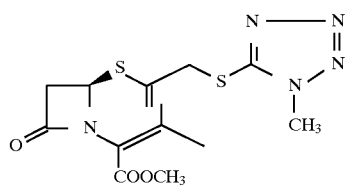 (7)
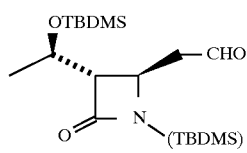 (8)
TBDMS:tert-butyldimethylsilyl
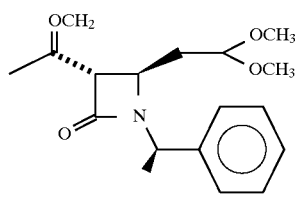 (9)
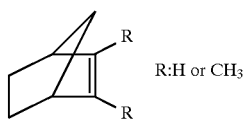 R:H or CH₃ (10)
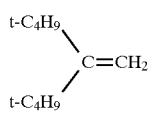 (11)
-continued
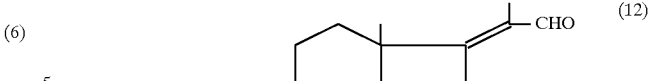 (12)
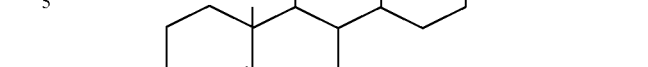 (13)
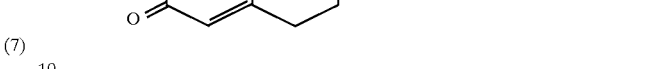 (14)
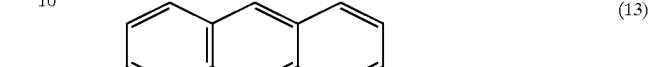 (15)
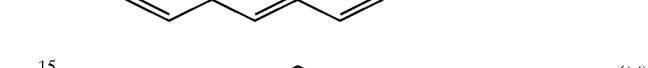 (16)
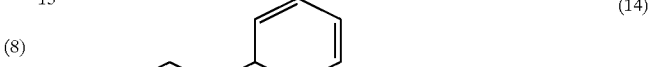 (17)
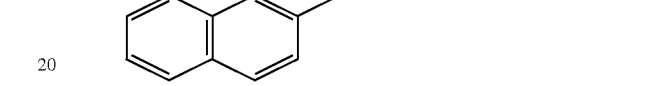 (18)
TABLE 3
| Ex. | Starting material | Reaction condition | Reducing agent | Product |
|---|---|---|---|---|
| 22 | (1) | O₃/−78° C., CH₂Cl₂ + CH₃OH | (A) | C₂H₅CHO |
| 23 | (2) | O₃/−78° C., CH₂Cl₂ + CH₃OH | (B) | CH₃COCOOCH₃ |
| 24 | (3) | O₃/−78° C., CH₂Cl₂ + CH₃OH | (B) | C₆H₅COCOOH |
| 25 | (4) | O₃/−78° C., C₂H₅OH | (C) | 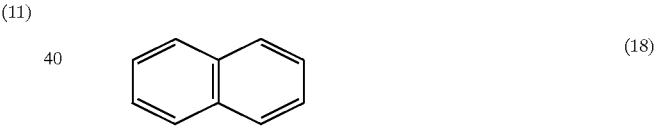 |

TABLE 3-continued

| Ex. | Starting material | Reaction condition | Reducing agent | Product |
|---|---|---|---|---|
| 26 | (5) | O$_3$/room temp., CH$_3$COOH | (E) | |
| 27 | (6) | O$_3$/−30° C., CH$_2$Cl$_2$ | (A) | |
| 28 | (7) | O$_3$/−15° C., CH$_2$Cl$_2$ + Isopropyl alcohol | (A) + (E) | |
| 29 | (8) | O$_3$/−15° C., CH$_2$Cl$_2$ + Isopropyl alcohol | (A) + (E) | |
| 30 | (9) | O$_3$/−15° C., CH$_2$Cl$_2$ + Isopropyl alcohol | (A) + (D) | |
| 31 | (10) | O$_3$/−15° C., CH$_3$OH | (C) | |
| 32 | (11) | O$_3$/−70° C., CH$_2$Cl$_2$ + CH$_3$OH | (C) | |
| 33 | (12) | O$_3$/−76° C., CH$_2$Cl$_2$ + Pyridine | (A) | |

TABLE 3-continued

| Ex. | Starting material | Reaction condition | Reducing agent | Product |
|---|---|---|---|---|
| 34 | (13) | $O_3$/–70° C., $CCl_4$ | (A) | |
| 35 | (14) | $O_3$/–30° C., $CH_3OH$ | (A) | |
| 36 | (15) | $O_3$/–25° C., $CHCl_3$ | (A) | |
| 37 | (16) | $O_3$/–30° C., $CH_2Cl_2$ + $CH_3OH$ | (A) + (D) | |
| 38 | (17) | $O_3$/–5° C., $CHCl_3$ | (D) | |
| 39 | (18) | $O_3$/–70° C., $CH_3OH$ | (A) | |

We claim:

1. A method of reducing an ozonide, comprising:

adding an ozonide reducing agent to an ozonide-containing solvent in an amount sufficient to reductively decompose the ozonide, said ozonide reducing agent being one or more compounds selected from the group consisting of a compound represented by the formula $$X—R^1—R^2—S—R^3—R^4—Y \qquad (1)$$

wherein $R^1$ and $R^4$ are the same or different and each represents a single bond or a straight- or branched-chain $C_{1-6}$ alkylene group; $R^2$ and $R^3$ are the same or different and each is a straight- or branched-chain $C_{1-6}$ alkylene group, a straight- or branched-chain $C_{2-8}$ alkenylene group, a straight- or branched-chain $C_{2-6}$ alkynylene group, a $C_{3-8}$ cycloaklylene group or a phenylene group which may have a $C_{1-6}$ alkyl group and/or an amino group as a substituent on the phenyl ring; X and Y are the same or different and each represents a hydroxyl group, a nitrile group or a carboxyl group; and a compound represented by the formula $$R^5—S—R^6 \qquad (2)$$

wherein $R^5$ and $R^6$ are the same or different and each represents thienyl, furyl, pyridyl, pyranyl, pyrrolyl, chromenyl, imidazolyl, pyrazolyl, thiazolyl, oxazolyl, pyrazinol, pyrimidyl, pyridazinyl, or quinolyl, having as a substituent at least one group selected from a hydroxyl group, a hydroxymethyl group, a nitrile group, a cyanomethyl group, a carboxyl group and a carboxymethyl group;

reductively decomposing the ozonide with said ozonide reducing agent; and removing the sulfoxide resulting from the ozonolysis reaction of said ozonide with said ozonide reducing agent.

2. The method of reducing an ozonide as defined in claim 1, wherein said ozonide reducing agent is a mixture of compounds of formulae (1) and (2).

3. The method of reducing an ozonide as defined in claim 1, wherein said ozonide reducing agent is thiodiethanol.

* * * * *